(12) United States Patent
Mitsuyoshi et al.

(10) Patent No.: US 11,147,487 B2
(45) Date of Patent: Oct. 19, 2021

(54) ESTIMATION METHOD, ESTIMATION PROGRAM, ESTIMATION DEVICE, AND ESTIMATION SYSTEM

(71) Applicants: PST CORPORATION, INC., Tokyo (JP); Shunji Mitsuyoshi, Tokyo (JP)

(72) Inventors: Shunji Mitsuyoshi, Tokyo (JP); Shuji Shinohara, Tokyo (JP)

(73) Assignee: PST CORPORATION, INC., Tokyo (JP)

( * ) Notice: Subject to any disclaimer, the term of this patent is extended or adjusted under 35 U.S.C. 154(b) by 23 days.

(21) Appl. No.: 16/074,351

(22) PCT Filed: Jan. 27, 2017

(86) PCT No.: PCT/JP2017/003003
§ 371 (c)(1),
(2) Date: Jul. 31, 2018

(87) PCT Pub. No.: WO2017/138376
PCT Pub. Date: Aug. 17, 2017

(65) Prior Publication Data
US 2019/0142323 A1    May 16, 2019

(30) Foreign Application Priority Data
Feb. 9, 2016 (JP) .............................. JP2016-022895

(51) Int. Cl.
*A61B 5/16* (2006.01)
*G10L 25/66* (2013.01)
*G10L 25/03* (2013.01)
*G10L 25/63* (2013.01)

(52) U.S. Cl.
CPC ................ *A61B 5/165* (2013.01); *A61B 5/16* (2013.01); *G10L 25/03* (2013.01); *G10L 25/63* (2013.01); *G10L 25/66* (2013.01)

(58) Field of Classification Search
CPC .............................. A61B 5/165; A61B 5/4803
USPC ......................................................... 600/300
See application file for complete search history.

(56) References Cited

U.S. PATENT DOCUMENTS

| | | | |
|---|---|---|---|
| 5,923,764 | A | 7/1999 | Shennib |
| 2009/0210220 | A1 | 8/2009 | Mitsuyoshi et al. |
| 2009/0313019 | A1 | 12/2009 | Kato et al. |
| 2010/0211394 | A1 | 8/2010 | Nazdratenko |

(Continued)

FOREIGN PATENT DOCUMENTS

| | | |
|---|---|---|
| CN | 101199002 A | 6/2008 |
| CN | 101346758 A | 1/2009 |

(Continued)

OTHER PUBLICATIONS

Jun. 25, 2019 Office Action issued in Canadian Patent Application No. 3,014,574.

(Continued)

*Primary Examiner* — Michael W Kahelin
(74) *Attorney, Agent, or Firm* — Oliff PLC (57) ABSTRACT

An estimation method and device comprising at least one feature amount is calculated with sound data uttered by a subject, a degree of a psychosomatic state of the subject is calculated based on the calculated feature amount, and the psychosomatic state of the subject are estimated based on the calculated degree.

8 Claims, 6 Drawing Sheets

CT

| | AUC | DECAY_POWER | DECAY_SLOPE_DIV | DECAY_SLOPE | DELTA_ZERO_MAX_ABS | DELTA_ZERO_DIV_ABS | PITCH_RATE | DELTA_ZERO_DIV |
|---|---|---|---|---|---|---|---|---|
| DECAY_POWER | 0.95 | | | | | | | |
| DECAY_SLOPE_DIV | 0.95 | -0.22 | | | | | | |
| DECAY_SLOPE | 0.93 | -0.19 | 0.69 | | | | | |
| DELTA_ZERO_MAX_ABS | 0.91 | -0.30 | -0.20 | -0.19 | | | | |
| DELTA_ZERO_DIV_ABS | 0.91 | -0.35 | -0.10 | -0.08 | 0.74 | | | |
| PITCH_RATE | 0.89 | -0.21 | 0.04 | 0.11 | 0.16 | 0.17 | | |
| DELTA_ZERO_DIV | 0.89 | -0.34 | -0.12 | -0.09 | 0.73 | 0.99 | 0.13 | |
| DECAY_COUNT | 0.89 | 0.19 | -0.72 | -0.58 | 0.11 | 0.04 | 0.02 | 0.04 |
| POWER_PEAK_COUNT | 0.88 | -0.24 | 0.72 | 0.62 | -0.16 | -0.04 | -0.09 | -0.05 |
| DECAY_POWER_DIV | 0.84 | 0.51 | -0.38 | -0.33 | -0.09 | -0.15 | -0.05 | -0.14 |
| ATTACK_SLOPE_DIV | 0.80 | -0.22 | 0.91 | 0.65 | -0.21 | -0.10 | -0.02 | -0.12 |
| ATTACK_SLOPE | 0.79 | -0.16 | 0.67 | 0.79 | -0.23 | -0.06 | 0.09 | -0.07 |
| ATTACK_COUNT | 0.77 | 0.24 | -0.49 | -0.49 | 0.08 | -0.01 | 0.10 | -0.01 |
| PITCH_TIME_CORRE | 0.71 | 0.15 | 0.00 | 0.00 | -0.12 | -0.11 | -0.20 | -0.11 |

(56) References Cited

U.S. PATENT DOCUMENTS

| | | | |
|---|---|---|---|
| 2011/0054361 A1 | 3/2011 | Sakoda et al. | |
| 2011/0295086 A1* | 12/2011 | Nakada | A61B 5/0496 600/301 |
| 2012/0116186 A1* | 5/2012 | Shrivastav | A61B 5/4803 600/301 |
| 2013/0080169 A1 | 3/2013 | Harada et al. | |
| 2013/0090927 A1* | 4/2013 | Quatieri | A61B 5/4803 704/249 |
| 2014/0243608 A1* | 8/2014 | Hunt | A61B 5/4088 600/300 |
| 2015/0142492 A1 | 5/2015 | Kumar | |
| 2015/0265206 A1* | 9/2015 | Sheinkopf | G10L 25/66 600/586 |
| 2015/0318002 A1* | 11/2015 | Karam | A61B 5/7264 704/231 |
| 2016/0015289 A1* | 1/2016 | Simon | A61B 5/1103 600/301 |
| 2016/0022167 A1* | 1/2016 | Simon | A61B 5/04842 600/301 |
| 2017/0000397 A1 | 1/2017 | Mitsuyoshi | |

FOREIGN PATENT DOCUMENTS

| | | |
|---|---|---|
| EP | 1300831 A1 | 4/2003 |
| JP | 2003-162294 A | 6/2003 |
| JP | 2004-317822 A | 11/2004 |
| JP | 2007-000280 A | 1/2007 |
| JP | 2010-506206 A | 2/2010 |
| JP | 2011-045520 A | 3/2011 |
| JP | 4851447 B2 | 1/2012 |
| JP | 2013-072979 A | 4/2013 |
| JP | 2013-183755 A | 9/2013 |
| JP | 2015-128579 A | 7/2015 |
| WO | 2006/132159 A1 | 12/2006 |

OTHER PUBLICATIONS

Shinichi Tokuno; "Stress Evaluation By Voice: From Prevention to Treatment in Mental Health Care"; pp. 1-7; Published Feb. 4, 2016.
Kakuichi Shiomi; "Voice Processing Technique for Human Cerebral Activity Measurement"; 2008 IEEE International Conference on Systems, Man and Cybernetics (SMC 2008); pp. 3343-3347.
Apr. 25, 2017 International Search Report issued in International Patent Application No. PCT/JP2017/003003.
Mitsuyoshi et al.; "Application of Sensibility Technology (ST) to Stress Detection"; Japanese Society of Fatigue Science Journal, vol. 6, No. 2; Mar. 2011; pp. 1-11.
Aug. 14, 2018 International Preliminary Report on Patentability issued in International Patent Application No. PCT/JP2017/003003.
Aug. 23, 2019 Office Action issued in Russian Patent Application No. 2018131306.
Sep. 2, 2019 Search Report issued in European Patent Application No. EP 17750101.2.
May 14, 2019 Office Action issued in Russian Patent Application No. 2018131306.
Dec. 5, 2019 Office Action issued in Taiwan Patent Application No. 106104120.
Apr. 30, 2020 Office Action issued in Canadian Patent Application No. 3,014,574.
Apr. 29, 2020 Office Action issued in Korean Patent Application No. 10-2018-7025687.
Jun. 2, 2020 Office Action issued in Chinese Patent Application No. 201780010227.6.
Oct. 23, 2020 Office Action issued in Indian Patent Application No. 201817026983.
Oct. 29, 2020 Office Action issued in Korean Patent Application No. 10-2018-7025687.
Jan. 18, 2021 Office Action issued in Chinese Patent Application No. 201780010227.6.
Jan. 22, 2021 Office Action issued in Canadian Patent Application No. 3,014,574.
The 23rd Diagnostic Accuracy Index and ROC-Nuclear Medicine Information Research Institute Study Group, Nuclear Medicine Dedication Information Study Group, 23rd Diagnostic Accuracy Index, pp. 1-4, Apr. 2, 2010.

* cited by examiner

| | AUC | DECAY_POWER | DECAY_SLOPE_DIV | DECAY_SLOPE | DELTA_ZERO_MAX_ABS | DELTA_ZERO_DIV_ABS | PITCH_RATE | DELTA_ZERO_DIV |
|---|---|---|---|---|---|---|---|---|
| DECAY_POWER | 0.95 | | | | | | | |
| DECAY_SLOPE_DIV | 0.95 | -0.22 | | | | | | |
| DECAY_SLOPE | 0.93 | -0.19 | 0.69 | | | | | |
| DELTA_ZERO_MAX_ABS | 0.91 | -0.30 | -0.20 | -0.19 | | | | |
| DELTA_ZERO_DIV_ABS | 0.91 | -0.35 | -0.10 | -0.08 | 0.74 | | | |
| PITCH_RATE | 0.89 | -0.21 | 0.04 | 0.11 | 0.16 | 0.17 | | |
| DELTA_ZERO_DIV | 0.89 | -0.34 | -0.12 | -0.09 | 0.73 | 0.99 | 0.13 | |
| DECAY_COUNT | 0.89 | 0.19 | -0.72 | -0.58 | 0.11 | 0.04 | 0.02 | 0.04 |
| POWER_PEAK_COUNT | 0.88 | -0.24 | 0.72 | 0.62 | -0.16 | -0.04 | -0.09 | -0.05 |
| DECAY_POWER_DIV | 0.84 | 0.51 | -0.38 | -0.33 | -0.09 | -0.15 | -0.05 | -0.14 |
| ATTACK_SLOPE_DIV | 0.80 | -0.22 | 0.91 | 0.65 | -0.21 | -0.10 | -0.02 | -0.12 |
| ATTACK_SLOPE | 0.79 | -0.16 | 0.67 | 0.79 | -0.23 | -0.06 | 0.09 | -0.07 |
| ATTACK_COUNT | 0.77 | 0.24 | -0.49 | -0.49 | 0.08 | -0.01 | 0.10 | -0.01 |
| PITCH_TIME_CORRE | 0.71 | 0.15 | 0.00 | 0.00 | -0.12 | -0.11 | -0.20 | -0.11 |

FIG. 5

| | DECAY_COUNT | POWER_PEAK_COUNT | DECAY_POWER_DIV | ATTACK_SLOPE_DIV | ATTACK_SLOPE | ATTACK_COUNT | PITCH_TIME_CORRE |
|---|---|---|---|---|---|---|---|
| DECAY_POWER | | | | | | | |
| DECAY_SLOPE_DIV | | | | | | | |
| DECAY_SLOPE | | | | | | | |
| DELTA_ZERO_MAX_ABS | | | | | | | |
| DELTA_ZERO_DIV_ABS | | | | | | | |
| PITCH_RATE | | | | | | | |
| DELTA_ZERO_DIV | | | | | | | |
| DECAY_COUNT | | | | | | | |
| POWER_PEAK_COUNT | -0.83 | | | | | | |
| DECAY_POWER_DIV | 0.33 | -0.38 | | | | | |
| ATTACK_SLOPE_DIV | -0.67 | 0.75 | -0.37 | | | | |
| ATTACK_SLOPE | -0.49 | 0.63 | -0.27 | 0.71 | | | |
| ATTACK_COUNT | 0.68 | -0.81 | 0.34 | -0.73 | -0.58 | | |
| PITCH_TIME_CORRE | -0.05 | -0.04 | 0.03 | 0.02 | -0.04 | 0.07 | |

FIG. 6

ESTIMATION METHOD, ESTIMATION PROGRAM, ESTIMATION DEVICE, AND ESTIMATION SYSTEM

CROSS REFERENCE TO RELATED APPLICATION

This application is a U.S. National Stage application claiming the benefit of prior filed International Application Number PCT/JP2017/003003, filed on Jan. 27, 2017, in which the International Application claims priority from Japanese Patent Application Number 2016-022895, filed on Feb. 9, 2016, the entire contents of which are incorporated herein by reference.

TECHNICAL FIELD

The present invention relates to an estimation method, an estimation program, an estimation device, and an estimation system for estimating health conditions of a subject.

BACKGROUND ART

It is known that the activity of a human brain (that is, an emotional state or a psychosomatic state of a person) is shown in sound uttered by the person. For example, it is proposed a technique which calculates a pitch frequency and the like from signal of sound uttered by a person and which estimates the emotional state (or the psychosomatic state) of the person based on information on a correspondence relation between the emotional state and the pitch frequency and the like, and based on parameters such as the calculated pitch frequency and the like (for example, see Patent Document 1).

Patent Document 1: International Publication No. 2006/132159

DISCLOSURE

PROBLEMS TO BE SOLVED

The correspondence relation between the emotional state and the parameters such as a pitch frequency is generated by causing each of a plurality of persons to determine the emotional state (for example, joy, anger, and the like) of a person who has uttered sound of each sample data, with the sample data of the uttered sound in various situations and scenes. That is, the generation of the correspondence relation between the emotional state and the parameters such as a pitch frequency requires time because as much sample data as possible is prepared in advance and the emotional state of the uttering person is determined by each of the plurality of persons for each sample data. In addition, each of the plurality of persons subjectively determines the emotional state, and thus the emotional state or the psychosomatic state which is estimated based on the correspondence relation between the emotional state and the parameters such as a pitch frequency are lacking in objectivity.

In addition, various threshold values for estimating the emotional state from the parameters are set for the generated correspondence relation. However, there is a problem in that the threshold values to be set are easily influenced by noise included in sound data and deterioration in sound quality due to processing, such as down sampling, which is performed on the sound data.

In an aspect, propositions of an estimation method, an estimation program, an estimation device, and an estimation system according to this disclosure are to provide a technique capable of estimating psychosomatic state of a subject more easily than in the related art, without previously preparing information indicating a correspondence relation between emotional state and parameters such as a pitch frequency.

Means for Solving the Problems

An estimation method according to an aspect includes calculating at least one feature amount with sound data uttered by a subject, calculating a degree of a psychosomatic state of the subject based on the calculated feature amount, and estimating the psychosomatic state of the subject based on the calculated degree.

An estimation program according to another aspect causes a computer to execute a process calculating at least one feature amount with sound data uttered by a subject, calculating a degree of a psychosomatic state of the subject based on the calculated feature amount, and estimating the psychosomatic state of the subject based on the calculated degree.

An estimation device according to still another aspect includes a first calculation unit calculating at least one feature amount with sound data uttered by a subject, a second calculation unit calculating a degree of a psychosomatic state of the subject based on the feature amount calculated by the first calculation unit, and an estimation unit estimating the psychosomatic state of the subject based on the degree calculated by the second calculation unit.

An estimation system according to still another aspect includes an acquisition device acquiring sound data uttered by a subject, and an estimation device including a first calculation unit which calculates at least one feature amount with the sound data acquired by the acquisition device, a second calculation unit which calculates a degree of a psychosomatic state of the subject based on the feature amount calculated by the first calculation unit, and an estimation unit which estimates the psychosomatic state of the subject based on the degree calculated by the second calculation unit.

According to the estimation method, the estimation program, the estimation device, and the estimation system of this disclosure, it is possible to estimate a psychosomatic state of a subject more easily than in the related art, without previously preparing information indicating a correspondence relation between an emotional state and parameters such as a pitch frequency.

DETAILED DESCRIPTION OF THE EMBODIMENTS

Hereinafter, an embodiment will be described with reference to the accompanying drawings.

Figure 1:
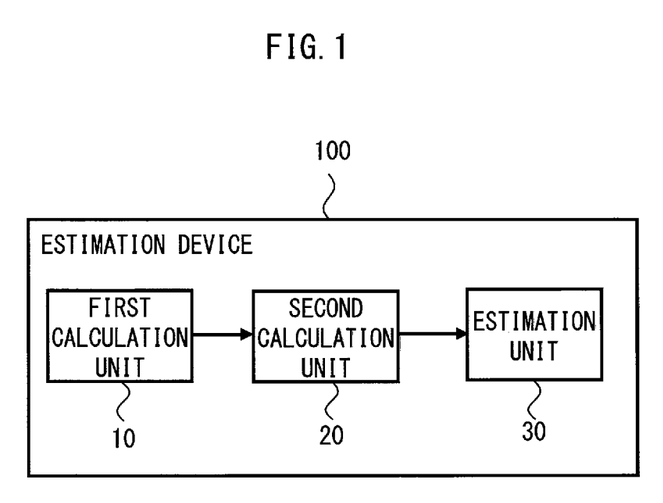
FIG. 1 is a diagram illustrating an estimation device according to an embodiment.

FIG. 1 illustrates an estimation device and an estimation method according to an embodiment.

An estimation device 100 illustrated in FIG. 1 is a computer device that includes a computational processing device such as a central processing unit (CPU), and a storage device such as a hard disk drive, and the like. The estimation device 100 functions as a first calculation unit 10, a second calculation unit 20, and an estimation unit 30, for example, by executing an estimation program stored in the storage device by the computational processing device. Meanwhile, the first calculation unit 10, the second calculation unit 20, and the estimation unit 30 may be realized by hardware.

The first calculation unit 10 calculates the pitch frequency, intensity, and the like of sound with sound data uttered by a subject which is stored in the storage device of the estimation device 100 or sound data of the subject which is acquired through a portable communication terminal such as a smart phone. The first calculation unit 10 calculates the frequency of detection of a pitch frequency in the utterance of the subject, an increase in the intensity (or the rate of decrease) of sound, and the like based on time changes in the pitch frequency, the intensity of sound, and the like. The frequency of detection of the pitch frequency, the rate of increase in the intensity of the sound, and the like are examples of feature amounts of the sound.

Meanwhile, the first calculation unit 10 may calculate at least one of the frequency of detection of the pitch frequency and the rate of increase (or the rate of decrease) in the intensity of the sound.

The second calculation unit 20 calculates a degree of the psychosomatic state of the subject, based on a feature amount such as the frequency of detection of the calculated pitch frequency. For example, the second calculation unit 20 calculates a value obtained by adding the frequency of detection of the calculated pitch frequency, the rate of increase in the intensity of sound, and the like, as a degree (hereinafter, also referred to as a vitality) of psychosomatic state of the subject. Meanwhile, the second calculation unit 20 may set at least one of the frequency of detection of the pitch frequency, the rate of increase in intensity, and the like, as the vitality of the subject. In addition, the second calculation unit 20 may set a value obtained by performing weight-adding of the frequency of detection of the pitch frequency, the rate of increase in intensity, and the like, as the vitality of the subject.

The estimation unit 30 estimates psychosomatic state (for example, whether or not the subject is in a depressed state, or the like) of the subject based on the calculated vitality. The estimation device 100 outputs information indicating the psychosomatic state estimated by the estimation unit 30 to a display such as an external organic electro-luminescence (EL) display or a liquid crystal display.

Meanwhile, the configuration and operation of the estimation device 100 are not limited to the example illustrated in FIG. 1. For example, an estimation system may be configured by including the estimation device 100, a portable communication terminal such as a smart phone, and a display such as an organic EL display.

As described above, in the embodiment illustrated in FIG. 1, the estimation device 100 calculates feature amounts such as the frequency of detection of a pitch frequency in the utterance of a subject, the rate of increase in the intensity of sound, and the like with sound data of the subject, and calculates the vitality of psychosomatic state of the subject based on the calculated feature amounts. The estimation device 100 estimates psychosomatic state of the subject based on the calculated vitality. Thereby, the estimation device 100 can estimate the psychosomatic state of the subject more easily than in the related art, without previously preparing information indicating a correspondence relation between emotional state and parameters such as a pitch frequency. In addition, the vitality is calculated based on the calculated feature amounts, and thus the estimation device 100 can objectively evaluate the psychosomatic state of the subject. In addition, the estimation device 100 does not use the information indicating the correspondence relation between emotional state and parameters such as a pitch frequency, and thus has resistance to deterioration in sound quality such as noise.

Figure 2:
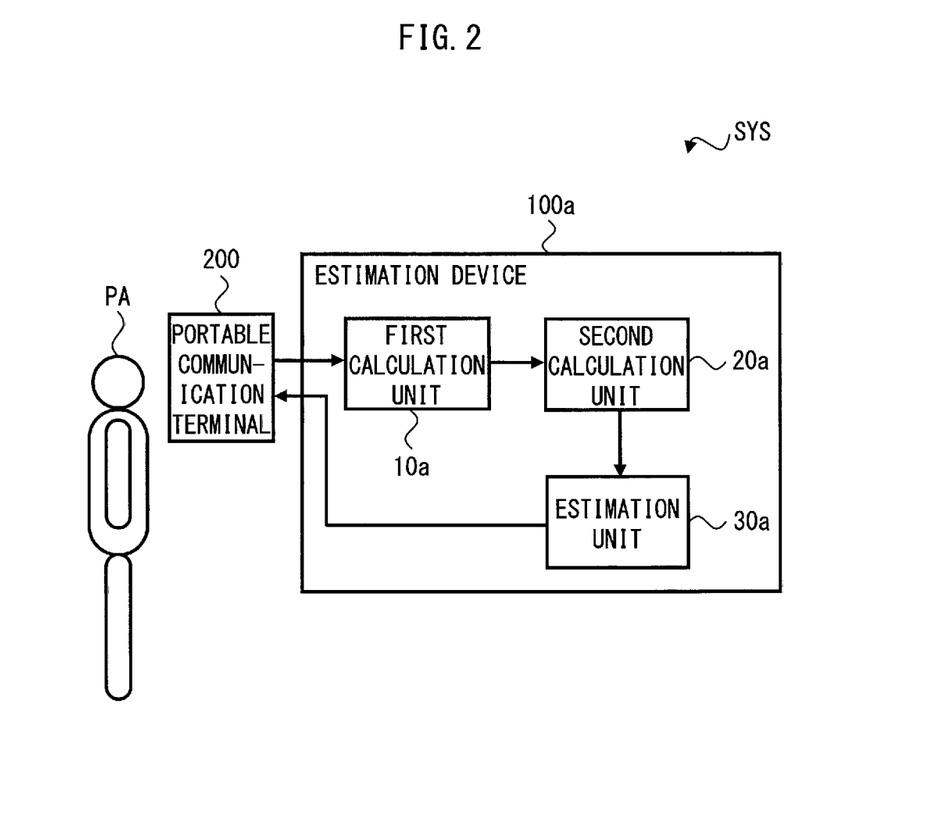
FIG. 2 is a diagram illustrating an estimation device according to another embodiment.

FIG. 2 illustrates an estimation method, an estimation device, and an estimation system according to another embodiment.

An estimation system SYS illustrated in FIG. 2 includes an estimation device 100a and a portable communication terminal 200. The estimation device 100a and the portable communication terminal 200 are connected to each other in a wired or wireless manner. Meanwhile, the estimation device 100a and the portable communication terminal 200 may be connected to each other through a network.

The portable communication terminal 200 is a mobile phone, a smart phone, or a tablet terminal. The portable communication terminal 200 acquires signal of sound uttered by a subject PA through a microphone included in the portable communication terminal 200, and samples the acquired signal at a predetermined sampling frequency (for example, 11 kilohertz, or the like) to generate sound data of a digital signal. The portable communication terminal 200 transmits the generated sound data to the estimation device 100a. In addition, the portable communication terminal 200 displays results of estimation performed by the estimation device 100a on a display, such as an organic EL display, which is included in the portable communication terminal 200. The portable communication terminal 200 is an example of an acquisition device.

Meanwhile, a microphone may be connected to the estimation device 100a in a wired or wireless manner, instead of the portable communication terminal 200. In this case, the estimation device 100a may sample signal of sound received from the microphone at a predetermined sampling frequency to generate sound data of a digital signal.

The estimation device 100a is a computer device including a computational processing device such as a CPU and a storage device such as a hard disk drive, or the like. The estimation device 100a functions as a first calculation unit 10a, a second calculation unit 20a, and an estimation unit 30a, for example, by executing an estimation program stored in the storage device by the computational processing device. Meanwhile, the first calculation unit 10a, the second calculation unit 20a, and the estimation unit 30a may be realized by hardware.

Meanwhile, the estimation device 100a may be realized in the portable communication terminal 200. That is, the CPU included in the portable communication terminal 200 executes an estimation program stored in the storage unit, such as a memory, which is included in the portable communication terminal 200, and thus the portable communication terminal 200 may function as the first calculation unit 10a, the second calculation unit 20a, and the estimation unit 30a.

The first calculation unit 10a calculates a pitch frequency, intensity, and the like of sound with the sound data of the subject PA which is acquired from the portable communication terminal 200. The first calculation unit 10a calculates feature amounts of the sound, such as the frequency of detection of a pitch frequency in the utterance of the subject PA and the rate of increase in the intensity of the sound, based on time changes in the calculated pitch frequency and intensity. Meanwhile, the operation of the first calculation unit 10a will be described with reference to FIG. 3.

The second calculation unit 20a calculates a degree (vitality) of the psychosomatic state of the subject PA based on the feature amounts, such as the frequency of detection of the pitch frequency, which are calculated by the first calculation unit 10a. The operation of the second calculation unit 20a will be described with reference to FIG. 4.

The estimation unit 30a estimates the psychosomatic state of the subject PA based on the degree calculated by the second calculation unit 20a. The estimation device 100a outputs the information on the psychosomatic state which are estimated by the estimation unit 30a to the portable communication terminal 200, and displays the information on the display, such as an organic EL display, which is included in the portable communication terminal 200.

Figure 3:
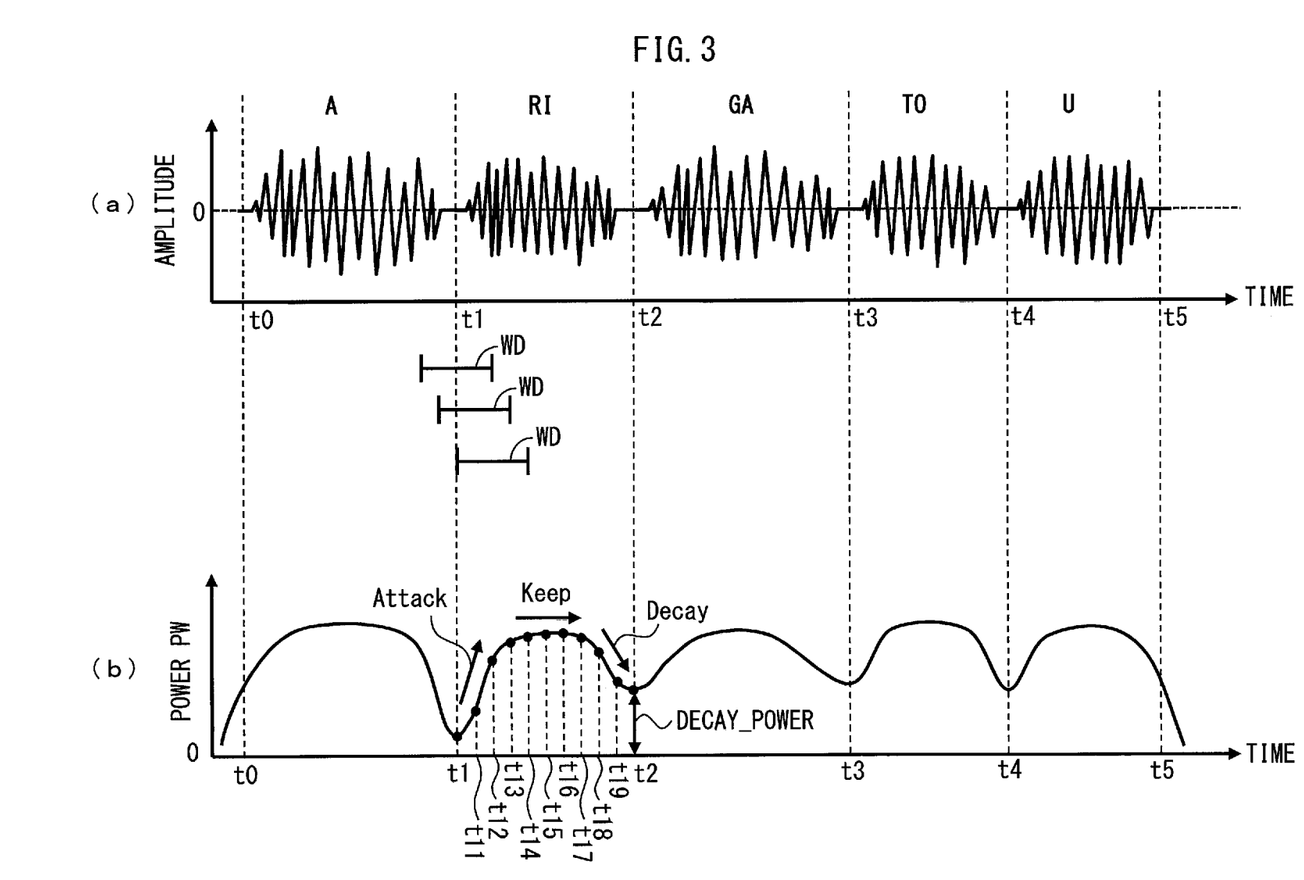
FIG. 3 is a diagram illustrating an example of sound data acquired through a portable communication terminal illustrated in FIG. 2.

FIG. 3 illustrates an example of sound data acquired through the portable communication terminal 200 illustrated in FIG. 2. (a) part of FIG. 3 illustrates time changes in the sound pressure of sound uttered by the subject PA acquired through the portable communication terminal 200, and (b) part of FIG. 3 illustrates time changes in the intensity of sound uttered by the subject PA. Meanwhile, the horizontal axis in FIG. 3 represents a time, the vertical axis in (a) part of FIG. 3 represents the sound pressure of sound, and the vertical axis in (b) part of FIG. 3 represents an intensity PW of the sound. The intensity PW of the sound is a square of the sound pressure.

FIG. 3 illustrates data in an utterance unit of an utterance of "ARIGATOU" (Thank you) in sound data of the utterance of the subject PA. Times t0, t1, t2, t3, and t4 represent a starting times of the utterance of words of "A", "RI", "GA", "TO", and "U" included in the utterance unit, respectively. Meanwhile, a description will be given of a process of calculating the first calculation unit 10a with respect to the sound data of the utterance of the word "RI" in the utterance unit of "ARIGATOU", but the first calculation unit 10a executes the calculation process with respect to the other words of "ARIGATOU" and other utterance units in the same or similar manner.

The first calculation unit 10a calculates a pitch frequency, an intensity, the number of zero point crossings, and the like for each window WD, for example, with the sound data acquired from the portable communication terminal 200. For example, the first calculation unit 10a executes spectrum analysis such as fast fourier transform (FFT) with the width of the window WD for each data of an utterance unit such as "ARIGATOU", with the acquired sound data, to thereby calculate a power spectrum. The first calculation unit 10a calculates the intensity PW of the sound by taking an average for each window WD because the value of the intensity PW of the sound which is calculated may vary significantly. That is, (b) part of FIG. 3 illustrates time changes in the intensity PW of the sound having been subjected to moving average processing.

In addition, the first calculation unit 10a executes autocorrelation processing on the calculated power spectrum and calculates a pitch frequency based on an interval between frequencies of adjacent maximum values (or minimum values) in the distribution of calculated autocorrelation coefficients. Further, the first calculation unit 10a calculates the number of times that a sound pressure of a waveform of sound crosses a reference pressure (for example, set to be "0") in sound data of each window WD, as the number of zero point crossings.

Meanwhile, the width of the window WD has the number of samplings such as 512, and the first calculation unit 10a moves the window WD at a predetermined interval such as a quarter of the width of the window WD to calculate a pitch frequency and the like by each window WD. That is, intensities PW at the times t1, t11, t12, t13, t14, t15, t16, t17, t18, t19, and t2 illustrated in (b) part of FIG. 3 indicate intensities calculated by the first calculation unit 10a with sound data of the utterance of the word "RI". Time intervals between the times t1, t11, t12, t13, t14, t15, t16, t17, t18, t19, and t2 are the same as a predetermined interval of the movement of the window WD.

In addition, the first calculation unit 10a may calculate parameters such as a pitch frequency F0 and a tempo from the sound data.

Next, the first calculation unit 10a calculates feature amounts, such as the frequency of detection of a pitch frequency in the utterance of the subject PA and the rate of increase in the intensity PW, based on the pitch frequency, intensity, the number of zero point crossings, and the like which are calculated for each utterance unit of "ARIGATOU". For example, the first calculation unit 10a calculates the ratio of windows WD for which a pitch frequency is calculated with respect to all of the windows WD as PITCH_RATE indicating the rate of detection of a pitch frequency, in each of the utterance units. That is, PITCH_RATE indicates the rate of utterance of a vocal sound (vowel) in sound of the subject PA. The first calculation unit 10a associates PITCH_RATE of each utterance unit with a time such as a starting time (for example, the time t0 in the case of "ARIGATOU") or a termination time (for example, the time t5 in the case of "ARIGATOU") of each utterance unit. The first calculation unit 10a acquires time changes of PITCH_RATE in the utterance of the subject PA.

In addition, the first calculation unit 10a calculates DELTA_ZERO_DIV indicating the degree of variations in each utterance unit of the number of zero point crossings Δ which is a difference in the number of zero point crossings between the adjacent windows WD with the calculated number of zero point crossings for each window WD. For example, the first calculation unit 10a obtains a difference in the number of zero point crossings between the windows WD adjacent to each other, and calculates a standard deviation of the obtained difference in the number of zero point crossings as DELTA_ZERO_DIV. Meanwhile, the first calculation unit 10a may calculate a dispersion value of the difference in the number of zero point crossings which is obtained between the windows WD as DELTA_ZERO_DIV. Alternatively, the first calculation unit 10a may calculate a value obtained by adding an absolute value of a difference between an average value of the differences in the number of zero point crossings between the windows WD and the difference in the number of zero point crossings between the windows WD, as DELTA_ZERO_DIV. The first calculation unit 10a associates DELTA_ZERO_DIV of each utterance unit with a time such as a starting time or an ending time of each utterance unit to acquire time changes in DELTA_ZERO_DIV in the utterance of the subject PA.

In addition, as illustrated in (b) part of FIG. 3, for example, in a utterance unit of "ARIGATOU", a time change in the intensity PW of each of the words "A", "RI", "GA", "TO", and "U" has an Attack region in which the intensity is increased, a Keep region in which the intensity is maintained constant, and a Decay region in which the intensity is decreased. Consequently, the first calculation unit 10a calculates an inclination of the intensity PW in the Attack region and the Decay region. For example, the first calculation unit 10a calculates an inclination $\delta AS$ of the intensity PW in the Attack region with an intensity PW (t1) at the time t1 and an intensity PW (t12) at the time t12, which are included in the Attack region in the intensity PW calculated in the word "RI", and Expression (1).

$$\delta AS = (PW(t12) - PW(t1))/(t12 - t1) \quad (1)$$

The first calculation unit 10a calculates an average value of the inclinations $\delta AS$ calculated in the words of "ARIGATOU", as an inclination ATTACK_SLOPE of the intensity PW in the Attack region of the utterance unit of "ARIGATOU". The first calculation unit 10a associates ATTACK_SLOPE of each utterance unit with a time such as a starting time or an ending time of each utterance unit to acquire time changes in ATTACK_SLOPE in the utterance of the subject PA.

Meanwhile, the first calculation unit 10a may calculate an inclination $\delta AS$ of an intensity PW in an Attack region of the word "RI" with an intensity PW (t1) at the time t1, an intensity PW (t11) at the time t11, and the intensity PW (t12) at the time t12. For example, the first calculation unit 10a calculates an inclination of an intensity between the intensity PW (t1) at the time t1 and the intensity PW (t11) at the time t11, and an inclination of an intensity between the intensity PW (t11) at the time t11 and the intensity PW (t12) at the time t12. The first calculation unit 10a calculates an average value of the inclinations of the calculated intensities, as the inclination MS of the intensity PW in the Attack region of the word "RI".

On the other hand, for example, the first calculation unit 10a calculates an inclination $\delta DS$ of an intensity PW in the Decay region with an intensity PW (t18) at the time t18 and an intensity PW (t2) at the time t2, which are included in the Decay region in the intensity PW calculated in the word "RI", and Expression (2).

$$\delta DS = (PW(t2) - PW(t18))/(t2 - t18) \quad (2)$$

The first calculation unit 10a calculates an average value of the inclination $\delta DS$ calculated in each word of "ARIGATOU", as an inclination DECAY_SLOPE of the intensity PW in the Decay region of the utterance unit of "ARIGATOU". The first calculation unit 10a associates DECAY_SLOPE of each utterance unit with a time such as a starting time or an ending time of each utterance unit to acquire time changes in DECAY_SLOPE in the utterance of the subject PA.

Meanwhile, the first calculation unit 10a may calculate the inclination $\delta DS$ of the intensity PW in the Decay region of the word "RI" with the intensity PW (t18) at the time t18, an intensity PW (t19) at the time t19, and the intensity PW (t2) at the time t2. For example, the first calculation unit 10a calculates an inclination of an intensity between the intensity PW (t18) at the time t18 and the intensity PW (t19) at the time t19, and an inclination of an intensity between the intensity PW (t19) at the time t19 and the intensity PW (t2) at the time t2. The first calculation unit 10a calculates an average value of the inclinations of the calculated intensities, as the inclination $\delta DS$ of the intensity PW in the Decay region of the word "RI".

In addition, the first calculation unit 10a calculates an average value of the intensities PW at the ending times t1, t2, t3, t4, and t5 of the utterance of each word of the utterance unit "ARIGATOU", as illustrated in (b) part of FIG. 3, as DECAY_POWER. The first calculation unit 10a associates DECAY_POWER of each utterance unit with a time such as a starting time or an ending time of each utterance unit to acquire time changes in DECAY_POWER in the utterance of the subject PA.

Meanwhile, the first calculation unit 10a may calculate feature amounts such as DECAY_SLOPE_DIV, DELTA_ZERO_MAX_ABS, DELTA_ZERO_DIV_ABS, DECAY_COUNT, and POWER_PEAK_COUNT. In addition, the first calculation unit 10a may calculate feature amounts such as DECAY_POWER_DIV, ATTACK_SLOPE_DIV, ATTACK_COUNT, and PITCH_TIME_CORRE.

Meanwhile, DECAY_SLOPE_DIV is a standard deviation, a dispersion value, or the like which indicates the degree of variations in DECAY_SLOPE in each utterance unit. DELTA_ZERO_MAX_ABS is an absolute value of the maximum DELTA_ZERO_DIV calculated using sound data having an intensity PW equal to or greater than a predetermined intensity among a plurality of values of DELTA_ZERO_DIV calculated in each utterance unit. DELTA_ZERO_DIV_ABS is an absolute value of DELTA_ZERO_DIV. DECAY_COUNT is the number of pieces of data sampled in the Decay region in the intensity PW of each utterance unit, as illustrated in (b) part of FIG. 3.

In addition, POWER_PEAK_COUNT is a number per unit time such as one second in which, for example, time changes in an intensity PW calculated in three windows WD adjacent to each other in each utterance unit. Meanwhile, the number of windows WD adjacent to each other may be three or more in calculating POWER_PEAK_COUNT. In addition, it is preferable that an intensity PW of each window WD is equal to or higher than a noise level.

In addition, DECAY_POWER_DIV is, for example, a standard deviation, a dispersion value, or the like which indicates the degree of variations in DECAY_POWER in each utterance unit. ATTACK_SLOPE_DIV is a standard deviation, a dispersion value, or the like which indicates variations in ATTACK_SLOPE in each utterance unit. ATTACK_COUNT is the number of pieces of data sampled in the Attack region in the intensity PW of each utterance unit, as illustrated in (b) part of FIG. 3. PITCH_TIME_CORRE is a correlation coefficient between the order (that is, the elapse of time) of the windows WD and time changes in a pitch frequency when the windows WD are numbered in each utterance unit.

Figure 4:
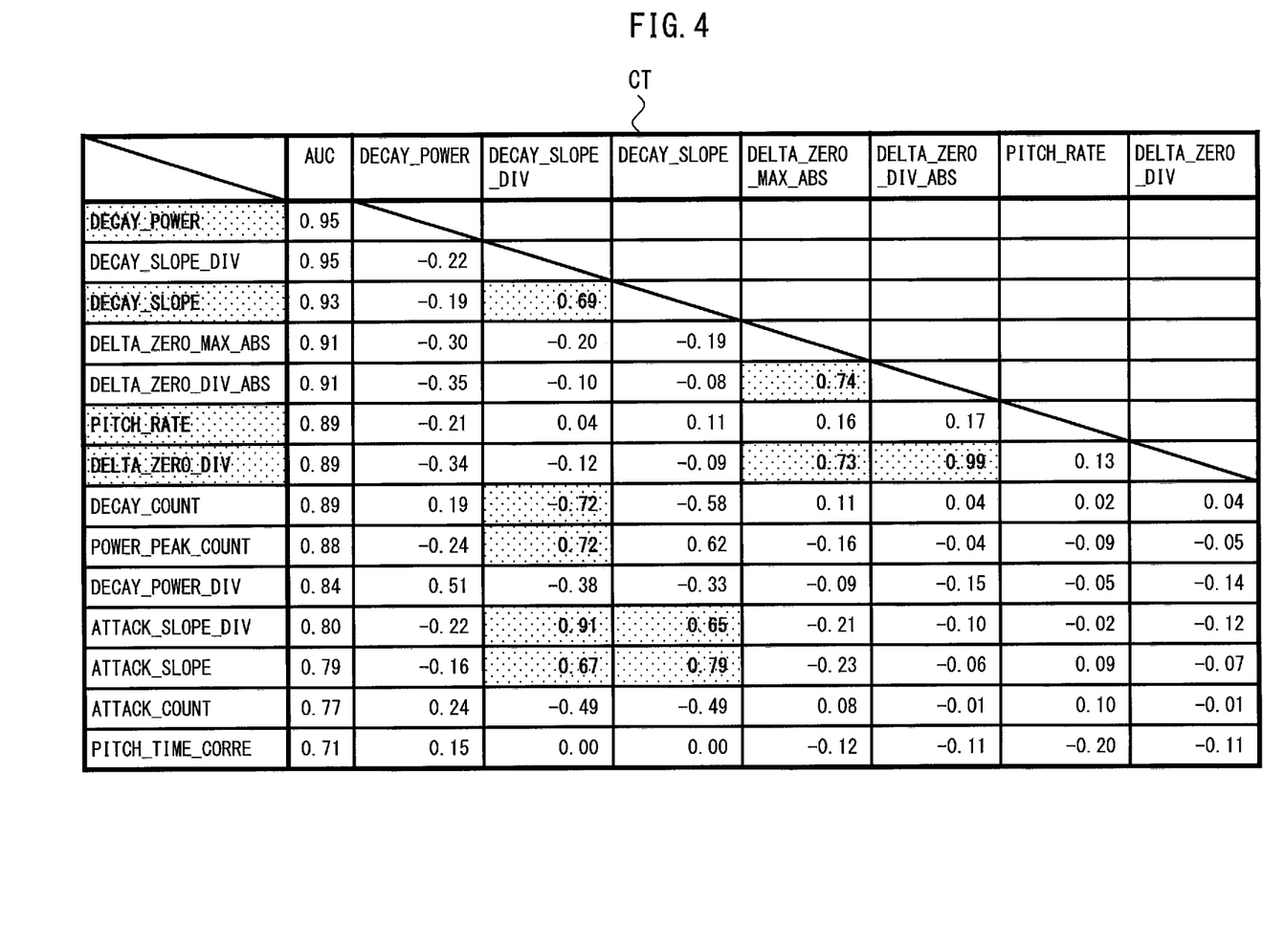
FIG. 4 is a diagram illustrating a correlation between feature amounts calculated by a first calculation unit 10a illustrated in FIG. 2.
Figure 5:
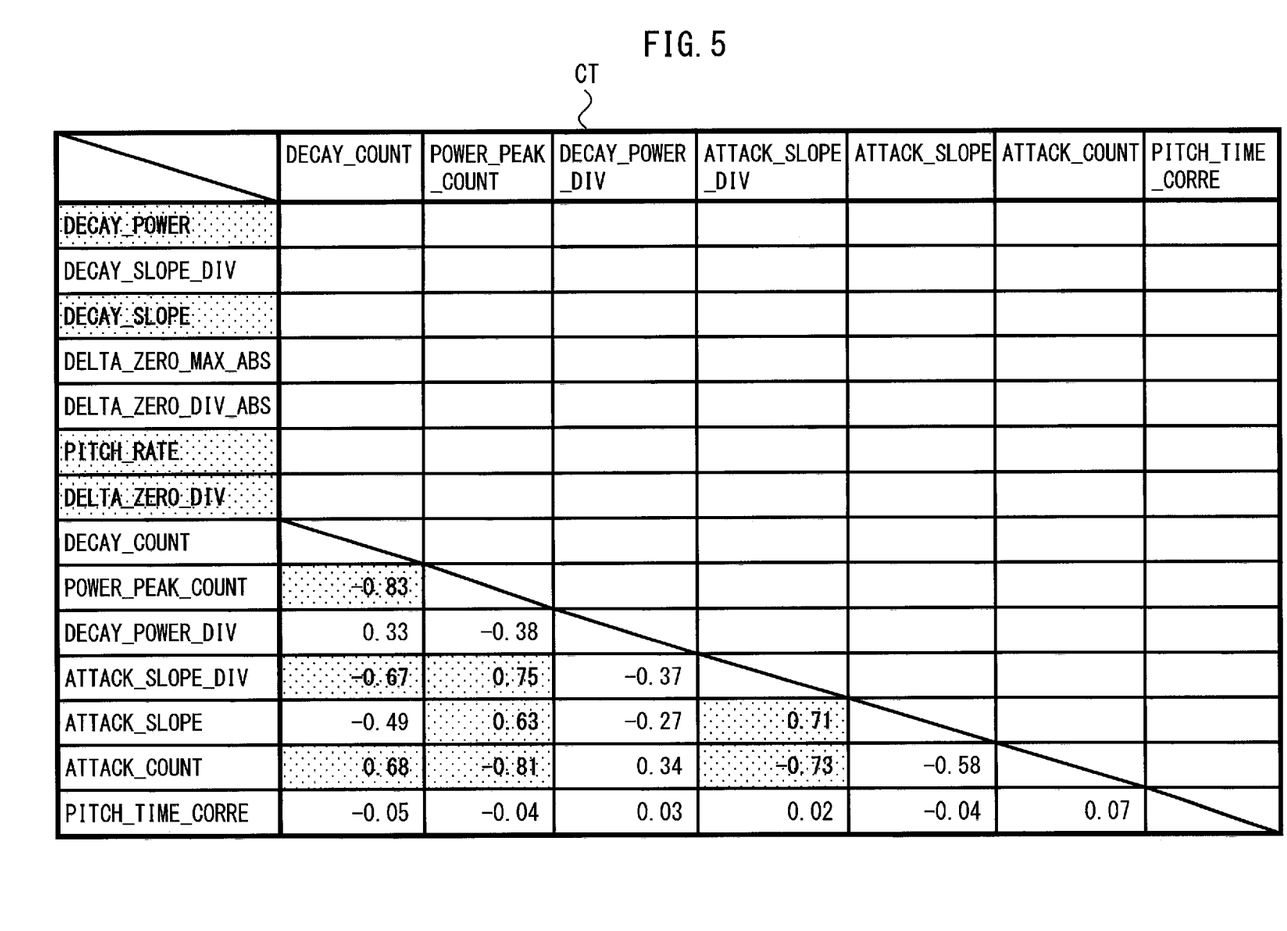
FIG. 5 is a diagram illustrating the continuation of the correlation between the feature amounts illustrated in FIG. 4.

FIGS. 4 and 5 illustrate a correlation between feature amounts calculated by the first calculation unit 10a illustrated in FIG. 2. A correlation table CT indicating a correlation between feature amounts has regions that respectively store a plurality of feature amounts such as LABEL, area under the curve (AUC), and DECAY_POWER. A name indicating a feature amount such as DECAY_POWER is stored in a LABEL region.

An AUC region stores AUC with respect to an ROC curve when a plurality of pieces of subject sound data, for example, which is given a label (for example, whether or not the subject is in a depressed state, whether the subject has cerebral infarction, or the like) by a doctor are classified using feature amounts in the LABEL region. That is, the value of the stored AUC indicates the degree of ability for determining psychosomatic state of the subject PA that each feature amount has. Meanwhile, ROC is short for Receiver Operating Characteristic.

That is, for example, it is indicated that it is possible to correctly determine psychosomatic state of the subject PA with a feature amount having the value of AUC being equal to or greater than 0.7 even when the feature amount is independently used, and it is not possible to correctly determine psychosomatic state of the subject PA with a feature amount having the value of AUC being smaller than 0.7 when the feature amount is independently used. In the correlation table CT, feature amounts having the value of AUC being equal to greater than 0.7 are shown.

In each of the regions of the plurality of feature amounts (hereinafter, also referred to as feature amount regions), a correlation coefficient between time changes indicated by a feature amount in each feature amount region, which is calculated using sound data of the subject PA, and time changes indicated by each feature amount in the LABEL region is stored. Meanwhile, in the correlation table CT illustrated in FIGS. 4 and 5, a feature amount region indicating that an absolute value of the correlation coefficient is equal to or greater than a predetermined threshold value, for example, 0.65 is shown as a hatched portion. This indicates that it is possible to estimate any one feature amount, out of the feature amount in the feature amount region and the feature amount in the LABEL region which indicate that the absolute value of the correlation coefficient is equal to or greater than a predetermined coefficient value, when the estimation device 100*a* calculates the other feature amount with the sound data of the subject PA. That is, it is indicated that the estimation device 100*a* calculates some feature amounts among the feature amounts in the LABEL regions of the correlation tables CT illustrated in FIGS. 4 and 5, which is the same as the calculation of all of the feature amounts in the LABEL region.

Consequently, the estimation device 100*a* selects a feature amount having the value of AUC being equal to or greater than 0.7 which is large and having no correlation with other feature amounts or a feature amount having a correlation with other feature amounts smaller than a predetermined coefficient value, among the feature amounts in the LABEL region, based on the correlation tables CT illustrated in FIGS. 4 and 5. For example, the estimation device 100*a* selects four feature amounts of DECAY_POWER, DECAY_SLOPE, PITCH_RATE, and DELTA_ZERO_DIV which are shown as hatched portions in the LABEL region.

Meanwhile, the estimation device 100*a* may select a feature amount having the value of AUC equal to or greater than 0.7 and having no relation or low relation with other feature amounts with a principal component analysis method or a neural network such as an autoencoder.

The first calculation unit 10*a* calculates the selected feature amounts of DECAY_POWER, DECAY_SLOPE, PITCH_RATE, and DELTA_ZERO_DIV with the sound data of the subject PA. The second calculation unit 20*a* performs weight-adding of the calculated feature amounts of DECAY_POWER, DECAY_SLOPE, PITCH_RATE, and DELTA_ZERO_DIV with Expression (3) to calculate a degree (vitality) cc of psychosomatic state of the subject PA.

$$\alpha = -\text{DECAY\_POWER} + \text{DECAY\_SLOPE} + \text{PITCH\_RATE} + 0.5 \times \text{DELTA\_ZERO\_DIV} \quad (3)$$

Meanwhile, weighting coefficients of the feature amounts of DECAY_POWER, DECAY_SLOPE, PITCH_RATE, and DELTA_ZERO_DIV are not limited to the case of Expression (3). For example, it is preferable that a weighting coefficient of each feature amount is appropriately set in accordance with the occupation, family structure, living environment, or the like of the target subject PA. For example, the second calculation unit 20*a* may calculate the vitality α of the subject PA with Expression (4). Meanwhile, the coefficient of DECAY_SLOPE in Expression (4) is "0".

$$\alpha = -0.5 \times \text{DECAY\_POWER} + \text{PITCH\_RATE} + 0.5 \times \text{DELTA\_ZERO\_DIV} \quad (4)$$

Meanwhile, each of the feature amounts of DECAY_POWER, DECAY_SLOPE, PITCH_RATE, and DELTA_ZERO_DIV may be substituted for a feature amount indicating a predetermined coefficient value, for example, a correlation coefficient equal to or greater than 0.65. For example, a correlation coefficient between DECAY_SLOPE and ATTACK_SLOPE is 0.79, and thus the first calculation unit 10*a* may calculate ATTACK_SLOPE instead of DECAY_SLOPE. The second calculation unit 20*a* calculates the vitality α with ATTACK_SLOPE together with DECAY_POWER, PITCH_RATE, DELTA_ZERO_DIV, and Expression (3). Meanwhile, it is preferable that a weighting coefficient of ATTACK_SLOPE is appropriately set.

In addition, the vitality α may be calculated using any one of the feature amounts such as DECAY_POWER, DECAY_SLOPE, PITCH_RATE, and DELTA_ZERO_DIV which have a high value of AUC.

Meanwhile, DECAY_POWER_DIV and PITCH_TIME_CORRE have the lowest value of AUC as compared to other feature amounts in spite of having a low correlation with other feature amounts, and thus are not included in Expression (3) for calculating the vitality α. However, DECAY_POWER_DIV and PITCH_TIME_CORRE are calculated by the first calculation unit 10*a* and may be included in Expression (3).

The estimation unit 30*a* estimates psychosomatic state of the subject PA, for example, whether or not the subject PA is in a depressed state, based on comparison between the vitality α calculated by the second calculation unit 20*a* and a threshold value. For example, the estimation unit 30*a* estimates that the subject PA has bad psychosomatic state (for example, a depressed state) when the vitality α is smaller than the threshold value (that is, sound uttered by the subject PA is not clear and inarticulate). On the other hand, the estimation unit 30*a* estimates that the subject PA has good psychosomatic state and is healthy when the vitality α is equal to or greater than the threshold value (that is, sound uttered by the subject PA is clear and articulate).

Meanwhile, the threshold value used by the estimation unit 30*a* is set based on, for example, a point on an ROC curve of the vitality α for minimizing a distance from a point at which a sensitivity is "1" and a false positive rate (1-specificity) is "0". Alternatively, the threshold value may be set based on Youden Index indicating a distance (sensitivity+specificity−1) between the ROC curve of the vitality α and the ROC curve when AUC is 0.5, and the like.

Figure 6:
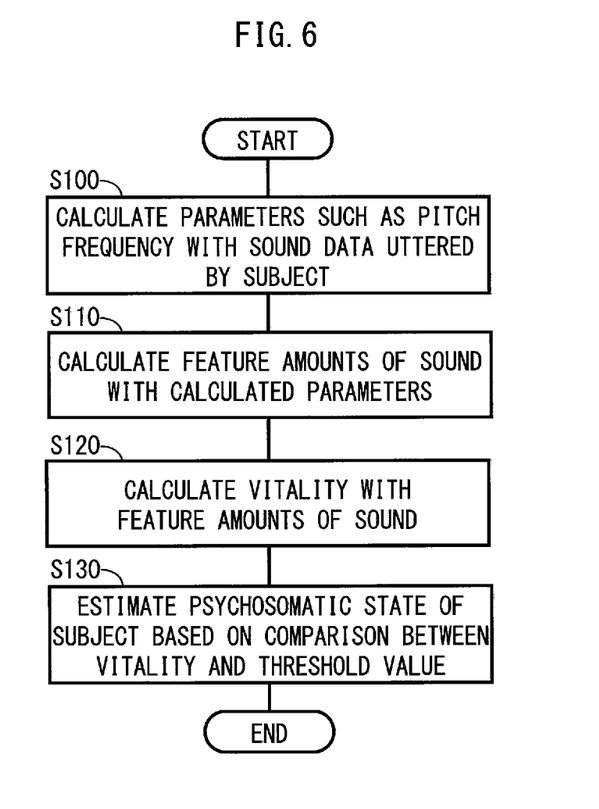
FIG. 6 is a diagram illustrating an example of an estimation process in an estimation system illustrated in FIG. 2.

FIG. 6 illustrates an example of an estimation process performed by the estimation device 100*a* illustrated in FIG. 2. Step S100 to step S130 are realized by executing an estimation program stored in the storage device of the estimation device 100*a* by a computational processing device mounted on the estimation device 100*a*. That is, FIG. 6 illustrates an estimation program and an estimation method according to another embodiment. In this case, the first calculation unit 10*a*, the second calculation unit 20*a*, and the estimation unit 30*a* which are illustrated in FIG. 2 are realized by executing the estimation program. Meanwhile, the process illustrated in FIG. 6 may be realized by hardware mounted on the estimation device 100*a*. In this case, the first calculation unit 10*a*, the second calculation unit 20a, and the estimation unit 30a which are illustrated in FIG. 2 are realized by a circuit disposed inside the estimation device 100a.

Meanwhile, the estimation program can be recorded in a removable disc such as a digital versatile disc (DVD) and can be distributed. In addition, the estimation program can be recorded in a portable storage medium such as a universal serial bus (USB) memory and can be distributed. Alternatively, the estimation device 100a may download the estimation program by a network through a network interface included in the estimation device 100a, and may be stored in a storage unit such as a memory.

In step S100, the first calculation unit 10a calculates parameters, such as a pitch frequency, an intensity, and the number of zero point crossings, for each window WD with sound data which is uttered by the subject PA and is acquired through the portable communication terminal 200.

In step S110, the first calculation unit 10a calculates feature amounts of DECAY_POWER, DECAY_SLOPE, PITCH_RATE, and DELTA_ZERO_DIV with the parameters, such as a pitch frequency, an intensity, and the number of zero point crossings, which are calculated in step S100.

In step S120, the second calculation unit 20a calculates the vitality $\alpha$ of the subject PA with the feature amounts calculated in step S110 and Expression (3).

In step S130, the estimation unit 30a estimates psychosomatic state of the subject PA (for example, where or not the subject PA is in a depressed state) based on comparison between the vitality $\alpha$ calculated in step S120 and a threshold value.

The estimation device 100a outputs information indicating the psychosomatic state estimated by the estimation unit 30a to the portable communication terminal 200, and displays the information on the display of the portable communication terminal 200. The estimation device 100a terminates the estimation process. The process illustrated in FIG. 6 is repeatedly executed whenever the subject PA utters toward the portable communication terminal 200.

As described above, in the embodiment illustrated in FIGS. 2 to 6, the estimation device 100a calculates feature amounts of DECAY_POWER, DECAY_SLOPE, PITCH_RATE, and DELTA_ZERO_DIV in the utterance of the subject with sound data of the subject PA. The estimation device 100a calculates the vitality $\alpha$ of psychosomatic state of the subject PA with the calculated feature amounts and Expression (3). The estimation device 100a estimates psychosomatic state of the subject based on comparison between the calculated vitality $\alpha$ and a threshold value. Thereby, the estimation device 100a can estimate psychosomatic state of the subject more easily than in the related art, without previously preparing information indicating a correspondence relation between emotional state and parameters such as a pitch frequency. In addition, the vitality $\alpha$ is calculated based on the calculated feature amounts, and thus the estimation device 100a can objectively evaluate the psychosomatic state of the subject PA. In addition, the estimation device 100a does not use the information indicating a correspondence relation between emotional state and parameters such as a pitch frequency, and thus has resistance to deterioration in sound quality such as noise.

Meanwhile, a description has been given when the estimation device 100 (100a) is applied to psychological counseling such as psychoanalysis, behavior prediction, or behavior analysis and an interview or prescription in psychiatric care or general medical care, but the invention is not limited thereto. For example, the estimation device 100 may be applied to a robot, artificial intelligence, a vehicle, a call center, entertainment, the Internet, a portable terminal device application or service of a smart phone, a tablet type terminal, or the like, and a retrieval system. In addition, the estimation device 100 may be applied to a diagnostic device, an automatic inquiry device, a disaster triage, and the like. In addition, the estimation device 100 may be applied to a financial credit management system, behavior prediction, a company, a school, a government agency, a police, the military, information analysis in information collection activity or the like, psychological analysis leading to false discovery, and organization group management. In addition, the estimation device 100 may be applied to a system for managing the health of the mind and behavior prediction of a member of an organization, a researcher, an employee, a manager, or the like, a system for controlling environment such as a house, an office, an airplane, or a spacecraft, or means for knowing the state of the mind or behavior prediction of a family member or a friend. In addition, the estimation device 100 may be applied to music, movie distribution, general information retrieval, information analysis management, information processing, or customer sensibility preference market analysis, a system that manages these through a network or on a stand-alone basis, and the like.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. An estimation device comprising:
a correlation table stored in a memory indicating a correlation between feature amounts and storing an area under the curve (AUC) in a receiver operating characteristic (ROC) curve when a plurality of pieces of subject sound data are classified using a plurality of feature amounts; and
a processor configured to function as:
a first calculation unit that
calculates the plurality of feature amounts with sound data uttered by a subject to be inspected, and
determines by referring to the correlation table, at least one feature amount having no relation with other feature amounts, and having the AUC of 0.7 or more, among the calculated plurality of feature amounts;
a second calculation unit that
applies a weighting coefficient of the feature amount determined by the first calculation unit in accordance with an occupation, family structure or living environment of the subject to be inspected, and
calculates a degree of psychosomatic state of the subject to be inspected based on the feature amount determined by the first calculation unit with the weighting coefficient applied; and
an estimation unit that estimates the psychosomatic state of the subject to be inspected by comparing the degree calculated by the second calculation unit to a threshold value, with the estimation unit estimating the psychosomatic state is a bad state when the degree is smaller than the threshold value, and the psychosomatic state is a healthy state when the degree is larger than the threshold value.

2. The estimation device according to claim 1, wherein the second calculation unit applies the weighting coefficient of the feature amount determined by the first calculation unit in accordance with the family structure of the subject to be inspected.

3. A non-transitory storage medium storing an estimation program causing a computer to execute:
calculating a plurality feature amounts with sound data uttered by a subject to be inspected, and determining by referring to a correlation table stored in a memory which indicates a correlation between feature amounts and which stores an area under the curve (AUC) in a receiver operating characteristic (ROC) curve when a plurality of pieces of subject sound data are classified using a plurality of feature amounts, at least one feature amount having no relation with other feature amounts, and having the AUC of 0.7 or more, among the calculated plurality of feature amounts;
applying a weighting coefficient of the at least one feature amount determined by the determining in accordance with an occupation, family structure or living environment of the subject to be inspected, and
calculating a degree of psychosomatic state of the subject to be inspected based on the determined feature amount with the weighting coefficient applied; and
estimating the psychosomatic state of the subject to be inspected by comparing the calculated degree to a threshold value, with the psychosomatic state estimated to be a bad state when the degree is smaller than the threshold value, and the psychosomatic state estimated to be a healthy state when the degree is larger than the threshold value.

4. The non-transitory storage medium according to claim 3, wherein the applying the weighting coefficient of the at least one feature amount determined by the determining is in accordance with the family structure of the subject to be inspected.

5. An estimation method comprising:
calculating a plurality feature amounts with sound data uttered by a subject to be inspected, and determining by referring to a correlation table stored in a memory which indicates a correlation between feature amounts and which stores an area under the curve (AUC) in a receiver operating characteristic (ROC) curve when a plurality of pieces of subject sound data are classified using a plurality of feature amounts, at least one feature amount having no relation with other feature amounts and having the AUC of 0.7 or more, among the calculated plurality of feature amounts;
applying a weighting coefficient of the at least one feature amount determined by the determining in accordance with an occupation, family structure or living environment of the subject to be inspected, and
calculating a degree of psychosomatic state of the subject to be inspected based on the determined feature amount with the weighting coefficient applied; and
estimating the psychosomatic state of the subject to be inspected by comparing the calculated degree to a threshold value, with the psychosomatic state estimated to be a bad state when the degree is smaller than the threshold value and the psychosomatic state estimated to be a healthy state when the degree is larger than the threshold value.

6. The estimation method according to claim 5, wherein the applying the weighting coefficient of the at least one feature amount determined by the determining is in accordance with the family structure of the subject to be inspected.

7. An estimation system comprising:
an acquisition device acquiring sound data uttered by a subject to be inspected; and
a processor configured to function as:
a first calculation unit which calculates a plurality feature amounts with a correlation table stored in a memory indicating a correlation between feature amounts and storing an area under the curve (AUC) in a receiver operating characteristic (ROC) curve when a plurality of pieces of subject sound data are classified using a plurality of feature amounts and with the sound data acquired by the acquisition device, and which determines by referring to the correlation table, at least one feature amount having no relation with other feature amounts, and having the AUC of 0.7 or more, among the calculated plurality of feature amounts,
a second calculation unit which applies a weighting coefficient of the feature amount determined by the first calculation unit in accordance with an occupation, family structure or living environment of the subject to be inspected, and calculates a degree of a psychosomatic state of the subject to be inspected based on the feature amount determined by the first calculation unit with the weighting coefficient applied, and
an estimation unit which estimates the psychosomatic state of the subject to be inspected by comparing the degree calculated by the second calculation unit to a threshold value, with the estimation unit estimating the psychosomatic state is a bad state when the degree is smaller than the threshold value, and the psychosomatic state is a healthy state when the degree is larger than the threshold value.

8. The estimation system according to claim 7, wherein the second calculation unit applies the weighting coefficient of the feature amount determined by the first calculation unit in accordance with the family structure of the subject to be inspected.

* * * * *